United States Patent [19]

Hester, Jr.

[11] Patent Number: 4,547,499
[45] Date of Patent: Oct. 15, 1985

[54] 2,4-DIHYDRO-2(OMEGA-AMINOALKYL)-1H-[1,2,4]TRIAZOLO[3,4-C]BENZOXAZIN-1-ONE ANTI-ALLERGY DRUG COMPOUNDS, COMPOSITIONS AND USE

[75] Inventor: Jackson B. Hester, Jr., Comstock Township, Kalamazoo County, Mich.

[73] Assignee: The Upjohn Company, Kalamazoo, Mich.

[21] Appl. No.: 609,035

[22] Filed: May 10, 1984

[51] Int. Cl.$^4$ .................. A61K 31/535; C07D 498/04
[52] U.S. Cl. ..................................... 514/235; 544/101
[58] Field of Search ................... 544/101; 424/248.54

[56] References Cited

U.S. PATENT DOCUMENTS

| | | | |
|---|---|---|---|
| 3,846,421 | 11/1974 | Meguro et al. | 260/247.2 A |
| 3,850,951 | 11/1974 | Meguro et al. | 260/308 C |
| 3,987,052 | 10/1976 | Hester, Jr. | 260/308 R |
| 4,250,094 | 2/1981 | Hester, Jr. | 260/245.5 |

OTHER PUBLICATIONS

J. Chem. Soc., (London), 1928, Part II, "The Synthesis . . . 1,4-Benzisooxazines", by G. Newberry et al., pp. 3046–3050.

Zhurnal Organichesskoi Khimii, 2, (1966), pp. 1478–1482; (Eng. Trans. 2, pp. 1461–1464).

Primary Examiner—Robert W. Ramsuer
Attorney, Agent, or Firm—John T. Reynolds

[57] ABSTRACT 2,4-Dihydro-2-(omega-aminoalkyl)-1H-[1,2,4]triazolo[3,4-c][1,4]benzoxazin-1-ones of the formula

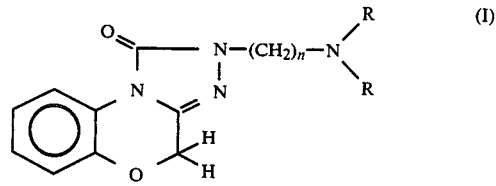

where n and -NRR are as defined in the specification, e.g., 2-[4-[4-(2,3-dihydro-2-oxo-1H-benzimidazol-1-yl)piperadinyl]butyl]-2,4-dihydro-1H-[1,2,4]triazolo[3,4-c][1,4]benzoxazin-1-one, are disclosed. They are useful for treating hypertension or allergy conditions in humans and valuable animals.

14 Claims, No Drawings

2,4-DIHYDRO-2(OMEGA-AMINOALKYL)-1H-[1,2,4]TRIAZOLO[3,4-C]BENZOXAZIN-1-ONE ANTI-ALLERGY DRUG COMPOUNDS, COMPOSITIONS AND USE

INTRODUCTION

This invention relates to a group of new 2,4-dihydro-2-(omega-aminoalkyl)-1H-[1,2,4]triazolo[3,4-c][1,4]benzoxazin-1-one compounds which are useful as anti-allergy and/or anti-hypertensive drugs in human and valuable animal patients.

BACKGROUND OF THE INVENTION

Triazolobenzodiazepine compounds such as alprazolam and triazolam are known. See, e.g., U.S. Pat. No. 3,987,052. 1-Dimethylaminomethyl triazolobenzodiazepines such as adinazolam are known. See, e.g., U.S. Pat. No. 4,250,094. Also, Meguro, et al., U.S. Pat. No. 3,850,951 discloses some triazolobenzodiazepine 5N- oxide compounds. However, all of the above compounds are disclosed as having their practical utility as central nervous system sedative, tranquilizer, muscle relaxant, sleep inducer, or anti-depressant drugs. Those references do not disclose or suggest the different polycyclic ring system of the compounds described and claimed herein or their use in the different field of anti-allergy and/or anti-hypertensive drugs.

OBJECTS OF THE INVENTION

It is an object of this invention to provide some new 2,4-dihydro-2-(omega-aminoalkyl)-1H-[1,2,4]triazolo[3,4-c][1,4]benzoxazin-1-ones as new compounds which are useful as drugs in anti-allergy and anti-hypertensive drug therapy programs.

It is also an object of the invention to provide pharmaceutical compositions containing one or more of the herein described 2,4-dihydro-2-(omega-aminoalkyl)-1H-[1,2,4]triazolo[3,4-c][1,4]benzoxazin-1-one compounds as the active anti-allergy and/or anti-hypertensive drug component in combination with one or more standard pharmaceutical formulation ingredients, which compositions are useful, when subdivided and packaged in pharmaceutical dosage unit form, for administration of an effective amount of the drug composition to a human or valuable animal suffering allergy and/or hypertensive conditions, to alleviate allergy and/or hypertensive symptoms in that patient.

It is also an object of this invention to provide a method for treating a human or valuable animal patient suffering allergy and/or hypertensive conditions involving administering to said patient an effective amount of a compound described and claimed herein to alleviate the allergy and/or hypertensive condition in said patient.

SUMMARY OF THE INVENTION

Briefly, this invention provides a group of 2,4-dihydro-2-(omega-aminoalkyl)-1H-[1,2,4]triazolo[3,4-c][1,4]benzoxazin-1-one compounds which are believed to be new. Examples of these compounds have been found to have hypotensive and anti-hypertensive drug activity in standard laboratory tests. The data indicate that these compounds are useful as drugs in humans and valuable animals for treating disease such as essential hypertension which is associated with elevated blood pressure. These compounds have also shown anti-anaphylactic activity and thus would be useful as drugs for treating human and valuable animal allergic conditions.

This invention also includes pharmaceutical compositions containing these compounds and a method for treating human and valuable animal patients suffering from essential hypertension or from an allergy condition with pharmaceutical compositions containing these compounds.

DETAILED DESCRIPTION OF THE INVENTION

More particularly this invention provides compounds of the formula (I), (See the attached Chemical Structure Sheet) where n is 3 or 4, the two R moieties are taken together with the nitrogen to which they are bonded to complete a ring system selected from the group consisting of ring moieties (a), (b), (c) or (d), as set forth on the Chemical Structure Sheet, where in ring moiety (c) $R_1$ is hydrogen, or a halogen having one atomic number of from 9 to 35, namely fluorine, chlorine or bromine, preferably in the 3- or 4-position of the phenyl ring, and in ring moiety (d) the $C_1$ to $C_3$-alkyl group can be methyl ethyl, n-propyl or isopropyl, or a pharmaceutically acceptable salt thereof.

Examples of such compounds include those named in the detailed examples which follow and the following compounds which can be prepared by analogous procedures.

2,4-Dihydro-2-[4-[4-(2-pyrimidinyl)-1-piperazinyl]-butyl]-1H-[1,2,4]triazolo[3,4-c][1,4]benzoxazin-1-one, 2-[4-[4-(2,3-Dihydro-2-oxo-1H-benzimidizol-1-yl)-1-piperidinyl]butyl]-2,4-dihydro-1H-[1,2,4]triazolo[3,4-c][1,4]benzoxazin-1-one, 2,4-Dihydro-2-[4-(4-phenylpiperazin-1-yl)butyl]-1H-[1,2,4]triazolo[3,4-c][1,4]benzoxazin-1-one, 2-[3-[4-(2,3-Dihydro-2-oxo-1H-benzimidazol-1-yl)piperidinyl]propyl]-2,4-dihydro-1H-[1,2,4]triazolo[3,4-c][1,4]benzoxazin-1-one, 2,4-Dihydro-2-[4-(4-isopropylpiperazin-1-yl)butyl]-1H-[1,2,4]triazolo[3,4-c][1,4]benzoxazin-1-one, 2,4-Dihydro-2-[4-(4-ethylpiperazin-1-yl)butyl]-1H-[1,2,4]triazolo[3,4-c][1,4]benzoxazin-1-one, 2,4-Dihydro-2-[4-(4-(3-fluorophenyl)piperazin-1-yl)butyl]-1H-[1,2,4]triazolo[3,4-c][1,4]benzoxazin-1-one, 2,4-Dihydro-2-[4-(3-bromophenyl)piperazin-1-yl)butyl]-1H-[1,2,4]triazolo[3,4-c][1,4]benzoxazin-1-one, 2,4-Dihydro-2-[3-(4-phenylpiperazin-1-yl)propyl]-1H-[1,2,4]triazolo[3,4-c][1,4]benzoxazin-1-one, and the like.

The compounds of Formula I can be prepard by the several step process outlined in the attached flow sheet Scheme I which summarizes in a generalized chemical reaction/product/chemical reaction/product/etc. form showing general structures and reactants for making the end product compounds (I).

Referring to the Scheme I flow sheet, the aminophenol starting materials II are either commercially available or have been described in the literature. Several examples of the compound III and IV type have been described in the literature. They can be prepared by literature methods. For example, the step A acylation reaction between the aminophenol and the chloroacetyl chloride can be carried out in dry acetone at 0° to 25° C. See G. Newberry, et al., "The Synthesis of Four Amino-3-hydroxy-1,4-benzisooxazines," in *J. Chem. Soc.* (London), 1928, p. 3046. The resulting chloroacetamide is warmed with dilute aqueous sodium hydroxide at 80°–100° C. to give lactam ring compound (III).

In optional step B, the shown thioketone (IV) is prepared by a modification of the method of A. I. Kiprianoo, et al., *Zhur. Org. Khim,* 2, 1478 (1966) [English translation, 2, 1461 (1966)]. A mixture of the lactam III and phosphorus pentasulfide in dry pyridine is warmed briefly at 125° C. to form the thioketone compound IV.

In step C, the thioketone (IV) is reacted with a $C_1$ to $C_6$-alkyl carbazate, in a lower alkanol ($C_1$ to $C_3$-alkanol) at about 20°–100° C. for a time sufficient to form the shown hydrazine derivative V. Ethyl carbazate is shown in Scheme I as the reactant in step C.

Compounds of Formula V can also be prepared by first treating the lactam compound (III) with triethyl oxoniumfluoroborate and then allowing the resulting imino ether (not shown) to react with a $C_1$ to $C_6$-alkyl carbazate in a lower alkanol solvent to form the hydrazine derivative compound V.

In step E, the triazolo ring compound (VI) is prepared by heating the Formula V compound at or above its melting point, usually at about 200°–250° C. to effect ring closure of the compound V to triazolo ring compound VI.

In step F the triazolo ring compound VI is alkylated with the selected omega-chloroalkyl bromide where n is 3 or 4, in the presence of sodium or potassium hydride as base, and N,N-dimethylformamide (DMF), N,N-dimethylacetamide (DMA) or N,N-dimethylsulfoxide (DMSO) as solvent for the reaction mixture to form the chloro-alkyl-triazolo compound VII.

In step G, the chloro-alkyl-triazolo compound VII is allowed to react with the selected amine (H-NRR) where -NRR denotes the amine of the selected amine groups (a), (b), (c), or (d) shown on the Chemical Structure Sheet, in a solvent such as DMF or DMA, usually at elevated temperatures such as 100°–150° C., optionally in the presence of potassium iodide to promote the reaction, for a time sufficient to form the compound of structure I. The amines of the groups (a), (b), (c), and (d) are either commercially available or have been described in the chemical literature.

The invention includes acid addition salts of the Formula I compounds. The salts can be used as an aid in extracting the Formula I compounds from their reaction mixtures. For this purpose acids such as oxalic, succinic, maleic acid salts of the Formula I compounds can be made and used. The invention also includes the usual pharmacologically and pharmaceutically acceptable acid addition salts of the Formula I compounds with acids such as hydrochloric, hydrobromic, hydroiodic, sulfamic, methanesulfonic, toluenesulfonic, maleic, itaconic, succinic acids, and the like.

This invention also relates to compositions containing a Formula I compound as an active ingredient in a pharmaceutical carrier. The compositions are useful in pharmaceutical dosage unit forms of the Formula I compounds for local (topical) and systemic administration (oral, rectal and parenteral administration form) in therapy for treating and alleviating hypertension and/or allergic conditions in humans and valuable animals, including dogs, cats and other commercially valuable and domestic animals.

The term "dosage unit form" as used in this specification and in the claims refers to physically discrete units suitable as unitary dosages for mammalian subjects, each unit containing a predetermined quantity of the essential active ingredient compound of this invention calculated to produce the desired effect, in combination with the required pharmaceutical means which adapt the said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification under preferred embodiments, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of the selected Formula I compound or salt thereof ingredients in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.5 mg. to about 350 mg. of the essential active ingredient per dosage unit form, which as aforesaid may be in the form of a semi-solid, topical or solid oral preparation, or a liquid oral or injectable preparation. The amount of the essential active Formula I compound, or pharmaceutically acceptable salt thereof, ingredient provided in the pharmaceutical dosage unit forms is that amount sufficient to obtain antihypertensive and/or anti-allergy effects within the aforesaid effective non-toxic range. Expressed otherwise, when used systemically, an amount of the essential active ingredient is provided to a recipient within a range from about 0.01 mg/kg. to about 5 mg./kg. of body weight of the recipient. Preferred dosages for most applications are 0.05 to 2.0 mg./kg. of body weight.

The useful pharmaceutical dosage unit forms of these compounds in pharmaceutical formulations is preferably adapted for oral administration to obtain anti-hypertensive and/or anti-allergy effects comprising an effective, non-toxic amount of a compound according to Formula I or as its pharmacologically acceptable salt.

Further the invention relates to methods of obtaining anti-hypertensive and/or anti-allergy effects in mammals, for example, human and valuable warm-blooded animals such as dogs, cats, horses and other commercially valuable animals, by administering systemically to the mammals the aforesaid Formula I compound or pharmaceutically acceptable salt thereof in pharmaceutical dosage unit forms supplying an effective, non-toxic amount of such compound for anti-hypertensive and/or anti-allergy effects.

The invention is further described and exemplified by the following detailed examples which are not intended to be limiting.

EXAMPLE 1

2,4-Dihydro-2-[3-[4-(2-pyrimidinyl)-1-piperazinyl]-propyl]-1H-[1,2,4]triazolo[3,4-c][1,4]benzoxazin-1-one (1) 2H-Benzoxazin-3-one A 2-aminophenol, in dry acetone, is acylated with chloroacetyl chloride at 0° to 25° C. to form the corresponding chloroacetamide, generally as described by procedures by G. Newberry, et al., in an article entitled "The Synthesis of Four Amino-3-Hydroxy-1,4-benzisooxazines" in J. Chem. Soc., London, 1928, Part II, pp. 3046-3050. The resulting chloroacetamide is warmed with dilute aqueous sodium hydroxide solution at 80°-100° C. to ring close the compound to form the benzoxazin-3-one (III).

(2) 3-(Ethoxycarbonylhydrazinyl)benzoxazine

The reagent/reactant triethyloxonium fluoroborate was prepared (Org. Syn., 46, 113) from 15.75 ml. (0.2 mole) of epichlorohydrin, dissolved in dry methylene chloride (300 ml.) cooled in an ice bath, and then the reagent/reactant was treated with the 2H-benzoxazin-3-one (lactam) from part 1 above (24.92 g., 0.167 mole). The ice bath cooling was removed and the resulting mixture was stirred at room temperature for 26 hours, cooled in an ice bath, and treated with 52.16 g. (0.501 mole) of ethyl carbazate in dry methanol, 75 ml. The ice bath cooling was removed and the mixture was stirred at room temperature for 2.5 hours and concentrated. The residue was poured into ice and water, stirred and filtered. The filter solid was washed well with water, dried in vacuo, and recrystallized from ethanol/ethyl acetate. (Note: Crystallizations from a two-solvent mixture of this type are generally carried out by dissolving the solid to be crystallized in a minimum amount of the solvent in which it is more soluble. The solvent is slowly evaporated, e.g., on a steam bath apparatus under a stream of nitrogen, while the solvent in which the solid is less soluble is slowly added until a saturated solution of the solid in the solvent mixture is obtained. This latter solution is then allowed to cool and the solid is allowed to crystallize therefrom). Here the first recrystallization solvent was ethanol, which was gradually replaced by ethyl acetate, to give 25.46 g. m.p. 185°-186.5° C. Concentration of the mother liquor gave 6.86 g. of a second crop, m.p. 184.5°-185.5° C. of the 3-(ethoxycarbonylhydrazinyl)benzoxazine.

(3)

2,4-Dihydro-1H-[1,2,4]triazolo[3,4-c][1,4]benzoxazin-1-one

An 8.85 g. (0.038 mole) portion of the 3-(ethoxycarbonylhydrazinyl)benzoxazine, from part 2 above was warmed at 230°-247° C. for 17 minutes under nitrogen atmosphere, in an oil bath which had been preheated to 230° C. The resulting melt was cooled and the resulting solid was recrystallized from ethyl acetate to give 2.0 g. of the named intermediate product, m.p. 197.5°-198.5° C. Concentration of the mother liquor gave 3.05 g. of a second crop, m.p. 196°-197.5° C.

Anal. calcd. for $C_9H_7N_3O_2$: % calcd: C, 57.14; H, 3.73; N, 22.21; % found: C, 57.16; H, 3.78; N, 22.13.

(4)

2-(3-Chloropropyl)-2,4-dihydro-1H-[1,2,4]triazolo[3,4-c][1,4]benzoxazin-1-one

A solution of 2,4-dihydro-1H-[1,2,4]triazolo[3,4-c][1,4]benzoxazin-1-one, from step 3 above (14.0 g., 0.074 mole), in 500 ml. of N,N-dimethylformamide (DMF) under a nitrogen atmosphere was treated with 3.91 g. (0.081 mole) of a 50% mineral oil suspension of sodium hydride and warmed on a steam bath for 0.5 hour. The resulting mixture was cooled in an ice bath, treated dropwise with 8.68 ml. (0.081 mole) of 1-bromo-3-chloropropane, and the resulting mixture was stirred 18 hours at room temperature to insure complete reaction and then concentrated in vacuo. The residue was mixed with cold water, extracted with methylene chloride, washed with dilute sodium chloride brine solution, dried over sodium sulfate and concentrated. The residue was chromatographed on 1000 g. of silica gel using 25% ethyl acetate in Skellysolve®B hexane (25:75, v/v) mixture. The product thus obtained was crystalized from ethyl acetate/Skellysolve®B hexanes, as described above to give in two crops 12.09 g., m.p. 77°-78° C., and 3.05 g., m.p. 76°-78° C., of the above subtitled intermediate product. The analytical sample had a melting point of 77.5°-78.5° C.

Anal. calcd. for $C_{12}H_{12}N_3O_2Cl$: % calcd: C, 54.24; H, 4.55; N, 25.82; Cl, 13.34; % found: C, 54.11; H, 4.61; N, 15.66; Cl, 13.35.

(5)

2,4-Dihydro-2-[3-[4-(2-pyrimidinyl)-1-piperazinyl]-propyl]-1H-[1,2,4]triazolo[3,4-c][1,4]benzoxazin-1-one A stirred solution of 5.41 g. (0.020 mole) of 2-(3-chloropropyl)2,4-dihydro -1H-[1,2,4]triazolo[3,4-c][1,4]benzoxazin-1-one, 5.02 g. (0.044 mole) of 1-piperazinecarboxaldehyde, and 3.23 g. (0.020 mole) of potassium iodide in 100 ml. of dry DMF, was warmed at 110° C. for 4 hours, cooled and concentrated. The residue was dissolved in dilute sodium bicarbonate in water solution and extracted with methylene chloride. The methylene chloride extracts were combined, washed with dilute sodium chloride brine solution, dried over sodium sulfate and concentrated to give 7.0 g. of a noncrystalline oil piperazinyl-intermediate, which was used in the following described chemical reaction without further purification.

A solution of the crude oil piperazinyl-intermediate from the above chemical reaction (6.86 g., 0.019 mole) in 100 ml. of 6N hydrochloric acid and 160 ml. of 95% ethanol was refluxed for 20 hours, cooled and concentrated.

The concentrate was mixed with cold 50% sodium hydroxide aqueous solution, saturated with sodium chloride and extracted with methylene chloride. The methylene chloride extracts were combined, washed with sodium chloride (brine) solution, dried over sodium sulfate and concentrated to give the desformyl derivative as the free base. A solution of this free base material in ethyl acetate was acidified to pH 3 with a hydrogen chloride in diethyl ether solution to form the hydrochloride salt. The solid hydrochloride salt which resulted was filtered, washed with ethyl acetate, dried and recrystallized from a methanol/ethyl acetate mixture in the manner described above to give three crops: 3.21 g., m.p. 227°–232° C.; 2.01 g., m.p. 227°–231° C.; and 0.102 g., m.p. 226.5°–231° C. of the salt. The mass spectrum analysis showed a molecular ion, (m+) at m/e 315 for the free base intermediate product.

The above acidified intermediate product was dissolved in saturated sodium bicarbonate in water solution and the pH was adjusted to 9 with 50% sodium hydroxide in water solution. The resulting aqueous solution was extracted with methylene chloride and the methylene chloride extracts were combined and washed with sodium chloride (brine) solution, dried over sodium sulfate, and concentrated to give 3.00 g. (0.009 mole) of the free base. A solution of this free base material, plus 1.09 g. (0.0095 mole) of 2-chloropyrimidine and 125 ml. of dry DMF was treated with 1.93 g. (0.014 mole) anhydrous potassium carbonate, and refluxed for 8.5 hours, cooled and concentrated. The resulting residue was dissolved in saturated sodium bicarbonate solution, saturated with sodium chloride and extracted with methylene chloride. The methylene chloride extracts were combined and washed with sodium chloride (brine), dried over sodium sulfate and concentrated. The residue was chromatographed on 250 g. of silica gel and eluted with 2% v/v diethylamine in ethyl acetate mixture. The titled product thus eluted was crystallized in the manner described above from an ethyl acetate/Skellysolve ®B mixture to give 1.98, m.p. 122°–123.5° C.

Anal. calcd. for $C_{20}H_{23}N_7O_2$: % calcd: C, 61.05; H, 5.98; N, 24.92; % found: C, 60.86; H, 5.82; N, 24.51.

EXAMPLE 2

2-[3-[4-(2,3-Dihydro-2-oxo-1H-benzimidazol-1-yl)-1-piperidinyl]propyl]-2,4-dihydro-1H-[1,2,4]triazolo-[3,4-c][1,4]benzoxazin-1-one A stirred solution of 1.33 g. (0.005 mole) of 2-(3-chloropropyl)2,4-dihydro-1H-[1,2,4]triazolo[3,4-c][1,4]benzoxazin-1-one, from Example 1, hereinabove, 0.83 g. (0.005 mole) of potassium iodide, and 2.39 g. (0.011 mole) of 4-(2-keto-1-benzimidazolinyl)piperadine in 25 ml. of DMF under a nitrogen atmosphere, was warmed to 105° C. for 4.75 hours. The solution was cooled, poured into cold sodium bicarbonate in water solution, and extracted with methylene chloride. The methylene chloride extracts were combined, washed with brine, dried over sodium sulfate and concentrated in vacuo. The resulting residue was chromatographed on 175 g. of silica gel and eluted with a 2% diethylamine/15% methanol/ethyl acetate, v/v/ mixture. The eluted product thus obtained was crystallized in the manner described in example 1, hereinabove, from a methylene chloride/methanol mixture to give in two crops 1.76 g., m.p. 176°–178° C. and 0.058 g., m.p. 175.5°–178° C. of the titled compound. The analytical sample had a melting point of 176.5°–177.5° C.

Anal. calcd. for $C_{24}H_{26}N_6O_3$: % calcd: C, 64.56; H, 5.87; N, 18.82; % found: C, 64.36; H, 6.25; N, 18.87; 64.38 6.07 18.53.

EXAMPLE 3

2,4-Dihydro-2-[3-(4-phenylpiperazin-1-yl)propyl]-1H-[1,2,4]triazolo[3,4-c][1,4]benzoxazin-1-one A stirred solution of 1.32 g. (0.005 mole) of 2-(3-chloropropyl)2,4-dihydro-1H-[1,2,4]triazolo[3,4-c][1,4]benzoxazin-1-one in 25 ml. of dry DMF was treated with 0.83 g. (0.005 mole) of potassium iodide and 1.78 g. (0.011 mole) of N-phenylpiperazine. The resulting mixture was kept at 50° C. for 18 hours, at 85° C. for 2 hours and at 105° C. for 2.5 hours. The mixture was then cooled, poured into ice water and extracted with methylene chloride. The methylene chloride extracts were combined, washed with dilute brine, dried over sodium sulfate and concentrated in vacuo. The resulting residue was chromatographed on 125 g. of silica gel and eluted therefrom with a 1.5% v/v methanol in chloroform mixture. The eluted product was crystallized in the manner described in example 1, hereinabove, from an ethyl acetate/Skellysolve ®B hexane mixture to give in two crops 0.74 g., m.p. 95°–96.5° C., and 0.37 g., m.p. 94°–96° C. of the titled compound. The analytical sample has a melting point of 96°–96.5° C.

Anal. calcd. for $C_{22}H_{25}N_5O_2$: % calcd: C, 67.50; H, 6.44; N, 17.89; % found: C, 67.49; H, 6.46; N, 18.17.

EXAMPLE 4

2-[4-[4-(2,3-Dihydro-2-oxo-1H-benzimidazol-1-yl)piperidinyl]butyl]-2,4-dihydro-1H-[1,2,4]triazolo[3,4-c][1,4]benzoxazin-1-one (1)

2-(4-Chlorobutyl)-2,4-dihydro-1H-[1,2,4]triazolo[3,4-c][1,4]benzoxazin-1-one

A solution of 2,4-dihydro-1H-[1,2,4]triazolo[3,4-c][1,4]benzoxazin-1-one (see example 1, part 3) (13.63 g.; 0.072 mole) in 500 ml. of DMF under a nitrogen atmosphere was treated with 3.79 g. (0.079 mole) of a 50% sodium hydride in oil suspension and the mixture was warmed on a steam bath for 0.5 hour. The mixture was cooled in an ice bath and treated with 9.11 ml. (0.079 mole) of 1-bromo-4-chlorobutane. The ice bath cooling was removed and the mixture was allowed to warm to room temperature and stirred for 18 hours. The mixture was concentrated in vacuo and the residue was poured into cold water, and extracted with methylene chloride. The methylene chloride extracts were combined and washed with dilute brine, dried over sodium sulfate and concentrated. The resulting residue was chromatographed through a column containing 850 g. of silica gel. The first product was eluted from the column with a 75% v/v ethyl acetate/Skellysolve ®B hexane mixture, and crystallized in the manner described in example 1, hereinabove, from an ethyl acetate/Skellysolve ®B hexane mixture to give in two crops 7.75 g., m.p. 56°–57° C. and 6.28 g., m.p. 54.5°–55.5° C. of 2-(4-chlorobutyl)-2,4-dihydro-1H-[1,2,4]triazolo[3,4-c][1,4]benzoxazin-1-one. The analytical sample had a melting point of 56°–56.5° C.

Anal. calcd. for $C_{13}H_{14}ClN_3O_2$: % calcd: C, 55.82; H, 5.04; N, 15.02; Cl, 12.57; % found: C, 54.66; H, 5.06; N, 14.54; Cl, 12.31.

The second product was eluted from the column with 3% v/v methanol in methylene chloride and crystallized in the manner described in example 1, hereinabove, from a methylene chloride/ethyl acetate mixture to give 0.55 g., m.p. 198°–201° C. and 0.10 g., m.p. 197.5°–200° C. of 2,2'-(4H,4'H)(1,4-butanediyl)bis-1H-[1,2,4]triazolo[3,4-c][1,4]benzoxazin-1-one. The analytical sample had melting point 199°–201° C.

Anal. calcd. for $C_{22}H_{20}N_6O_4$: % calcd: C, 61.10; H, 4.66; N, 19.43; % found: C, 60.75; H, 4.53; N, 19.76.

This second product was not further used in this process.

(2) The above-named end product.

A solution of 2-(4-chlorobutyl)-2,4-dihydro-1H-[1,2,4]triazolo[3,4-c][1,4]benzoxazin-1-one, (1.40 g., 0.005 mole), potassium iodide (0.83 g.; 0.005 mole) and 4-(2-keto-1-benzimidazolinyl)piperidine (2.39 g.; 0.011 mole) in 25 ml. of DMF was warmed to 115° C. and stirred for 4.75 hours. The resulting solution was cooled, poured into saturated sodium bicarbonate aqueous solution and extracted with methylene chloride. The methylene chloride extracts were combined and washed with brine solution, dried over sodium sulfate and concentrated in vacuo. The resulting residue was crystallized from ethyl acetate to give 1.87 g., m.p. 173°–175.5° C. and 0.03 g., m.p. 172°–173° C. of the above named end product. The analytical sample had melting point 174°–175.5° C.

Anal. calcd. for $C_{25}H_{28}N_6O_3$: % calcd: C, 65.20; H, 6.13; N, 18.25; % found: C, 65.02; H, 6.26; N, 18.19.

EXAMPLE 5

2,4-Dihydro-2-[4-(4-methylpiperazin-1-yl)butyl]-1H-[1,2,4]triazolo[3,4-c][1,4]benzoxazin-1-one, and its dihydrochloride salt A stirred solution of 2-(4-chlorobutyl)-2,4-dihydro-1H-[1,2,4]triazolo[3,4-c][1,4]benzoxazin-1-one, (1.40 g.; 0.005 mole), potassium iodide (0.83 g.; 0.005 mole) and N-methylpiperazine (1.10 g.; 0.011 mole) was warmed slowly to 100° C. and allowed to react for 18 hours. The solution was cooled, poured into ice water and extracted with methylene chloride. The methylene chloride extracts were combined and washed with dilute brine solution, dried over sodium sulfate and concentrated in vacuo. A solution of the resulting free base named product residue in methylene chloride was acidified with a hydrogen chloride/diethyl ether mixture and the resulting salt product was recrystallized in the manner described in example 1, hereinabove, from a methanol/ethyl acetate mixture to give 1.15 g., m.p. 258.5°–261° C. (dec.) and 0.22 g., m.p. 257°–260° C. (dec.) of the titled end product salt compound. The analytical sample had melting point 259°–261° C. (dec.).

Anal. calcd. for $C_{18}H_{26}Cl_2N_5O_2$: % calcd: C, 51.92; H, 6.54; N, 16.82; Cl, 17.03; % found: C, 51.65; H, 6.61; N, 16.70; Cl, 16.64.

EXAMPLE 6

2,4-Dihydro-2-[4-(4-phenylpiperazin-1-yl)butyl]-1H-[1,2,4]triazolo[3,4-c][1,4]benzoxazin-1-one A solution of 2-(4-chlorobutyl)-2,4-dihydro-1H-[1,2,4]triazolo[3,4-c][1,4]benzoxazin-1-one (see example 4, part 1), (1.40 g.; 0.005 mole), potassium iodide (0.83 g.; 0.005 mole) and N-phenylpiperazine (1.79 g.; 0.011 mole) was stirred at 100° C. for 5 hours. The reaction mixture was cooled, poured into water and extracted with methylene chloride. The methylene chloride extracts were combined, washed with dilute brine solution, dried over sodium sulfate and concentrated in vacuo. The resulting residue was chromatographed through 125 g. of silica gel, using a 2% v/v diethylamine in ethyl acetate as eluting liquid. The eluted product thus obtained, titled above, was crystallized in the manner described in example 1, hereinabove, from an ethyl acetate/Skellysolve ®B hexane mixture to give 1.56 g., m.p. 89°–90° C. and 0.115 g., m.p. 85°–87° C. of the named, titled compound hereinabove. The analytical sample had melting point 89°–90.5° C.

Anal. calcd. for $C_{23}H_{27}N_5O_2$: % calcd: C, 68.13; H, 6.71; N, 17.27; % found: C, 68.33; H 6.84; N, 17.53.

EXAMPLE 7

2-[4-[4-(3-Chlorophenyl)-1-piperazinyl]butyl]-2,4-dihydro-1H-[1,2,4]triazolo[3,4-c][1,4]benzoxazin-1-one A solution of 2-(4-chlorobutyl)-2,4-dihydro-1H-[1,2,4]triazolo[3,4-c][1,4]benzoxazin-1-one (see example 4, part 1), (1.5 g., 0.005 mole), the free base obtained from 1-(m-chlorophenyl)piperazine hydrochloride (1.17 g.; 0.006 mole), 1.38 g. (0.010 mole) of potassium carbonate, 0.83 g. (0.005 mole) of potassium iodide, and 30 ml. of dry DMF was kept at 130° C. for 5 hours, cooled, mixed with toluene and concentrated. Xylene was added and the resulting mixture was again concentrated. The resulting residue was mixed with toluene and concentrated again. The resulting residue was added to ice and water and extracted with methylene chloride. The methylene chloride extracts were combined, washed with brine, dried over sodium sulfate and concentrated. The resulting residue was chromatographed on silica gel (125 g.) column and elution initially was with 50% v/v ethyl acetate in Skellysolve ®B hexanes. This eluting solvent mixture eluted minor materials which had $R_f$ properties greater than that of the above named product. The named product was then eluted from the column with a 75% v/v ethyl acetate in Skellysolve ®B hexanes mixture solvent and crystallized in the manner described in example 1, hereinabove, from an ethyl acetate/Skellysolve ®B hexanes mixture to give 0.56 g., m.p. 133°–135° C. and 0.11 g., m.p. 132°–134° C. of the titled product. The analytical sample had melting point 133°–135° C.

Anal. calcd. for $C_{23}H_{26}ClN_5O_2$: % calcd: C, 62.79; H, 5.96; Cl, 8.06; N, 15.92; % found: C, 62.48; H, 5.93; Cl, 8.04; N, 16.03.

EXAMPLE 8

One thousand tablets for oral use, each containing 40 mg. of 2-[4-[4-(2,3-dihydro-2-oxo-1H-benzimidazol-1-yl)piperidinyl]butyl-2,4-dihydro-1H-[1,2,4]triazolo[3,4-c][1,4]benzoxazen-1-one, from example 4 above, as the essential active ingredient are prepared from the following ingredients:

| | |
|---|---|
| Essential active ingredient | 40 gm. |
| Dicalcium phosphate | 150 gm. |
| Methylcellulose, USP (15 cps.) | 6.5 gm. |
| Talc | 20 gm. |
| Calcium stearate | 2.0 gm. |

The essential active ingredient and dicalcium phosphate are mixed well, granulated with 7.5% aqueous solution of methylcellulose, passed through a No. 8 screen and dried carefully. The dried granules are passed through a No. 12 screen, mixed with the talc and stearate and compressed into tablets. These tablets are useful in the treatment of hypertension in adult humans at a dose of 1 tablet 1–4 times a day as needed.

EXAMPLE 9

One thousand two-piece hard gelatin capsules for oral use, each capsule containing 20 mg. of 2,4-dihydro-2-[4-(4-methylpiperazin-1-yl)butyl]-1H-[1,2,4]triazolo[3,4-c][1,4]benzoxazin-1-one (example 5) as the essential active ingredient are prepared from the following ingredients:

| Essential active ingredient | 20 gm. |
|---|---|
| Lactose, USP | 100 gm. |
| Starch, USP | 10 gm. |
| Talc, USP | 5 gm. |
| Calcium stearate | 1 gm. |

The finely powdered materials are mixed thoroughly, then filled into hard gelatin capsules of appropriate size.

One capsule 4 times daily is useful for the treatment of hypertension in adult humans.

EXAMPLE 10

One-piece soft elastic capsules for oral use, each containing 100 mg. of 2,4-dihydro-2-[4-(4-phenylpiperazin-1-yl)butyl]-1H-[1,2,4]triazolo[3,4-c][1,4]benzoxazin-1-one (example 6) as the essential active ingredient are prepared in the usual manner by first dispersing the active material in sufficient corn oil to render the material capsulatable.

One capsule two times daily is useful in the treatment of hypertension in adult humans.

EXAMPLE 11

An aqueous oral preparation containing in each teaspoonful (5 ml.) 80 mg. of 2-[4-[4-(3-chlorophenyl)-1-piperazinyl]butyl]-2,4-dihydro-1H-[1,2,4]triazolo[3,4-c][1,4]benzoxazin-1-one (example 7) as the essential active ingredient is prepared fom the following ingredients:

| Essential active ingredient | 160 gm. |
|---|---|
| Methylparaben, USP | 7.5 gm. |
| Propylparaben, USP | 2.5 gm. |
| Saccharin | 12.5 gm. |
| Glycerine | 3,000 ml. |
| Tragacanth powder | 10 gm. |
| Orange oil flavor | 10 gm. |
| Orange II | 7.5 gm. |
| Deionized water, q.s. to | 10,000 ml. |

The foregoing aqueous preparation is useful in the treatment of hypertension at a dose of 1 teaspoonful 4 times daily.

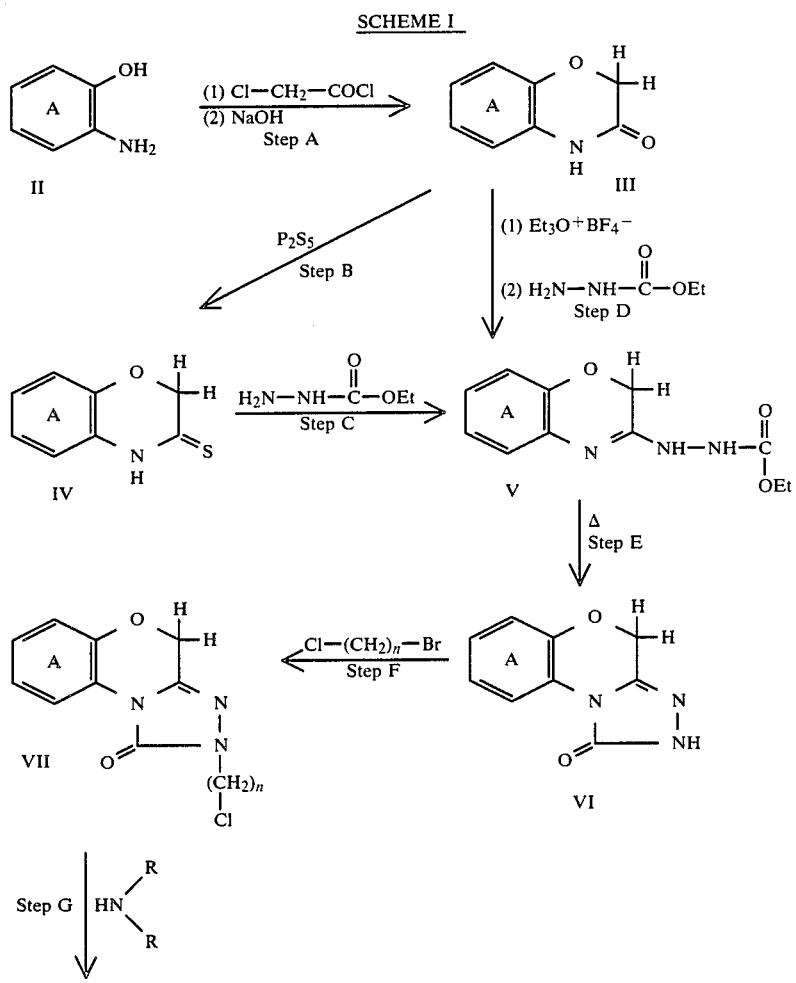

SCHEME I

SCHEME I

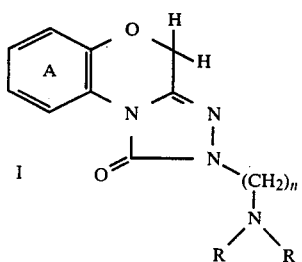

CHEMICAL STRUCTURE SHEET

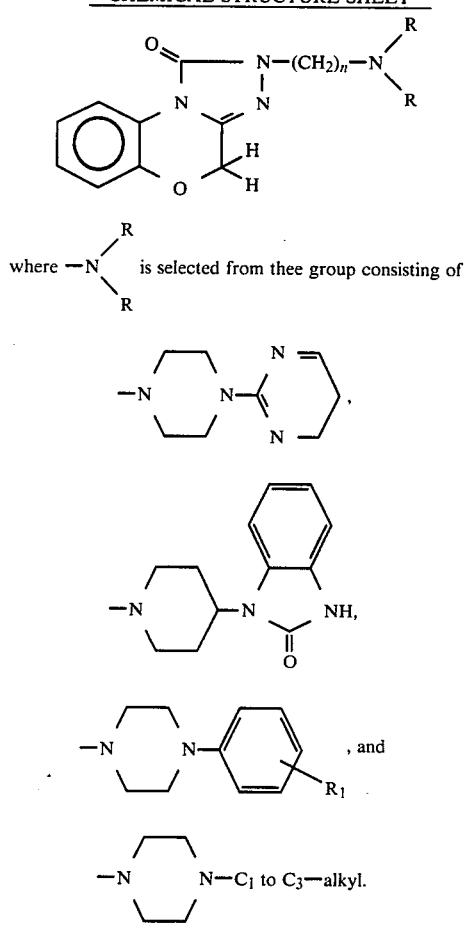

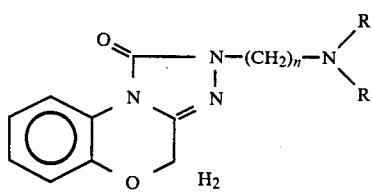

We claim:
1. A compound of the formula

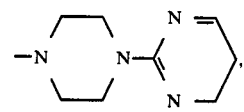

wherein n is 3 or 4;
the two R moieties are taken together with the nitrogen to which they are bonded to complete a ring system selected from the group consisting of

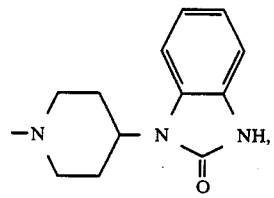

(a)

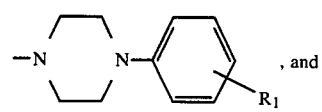

(b)

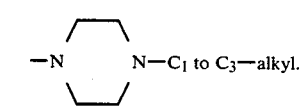

(c)

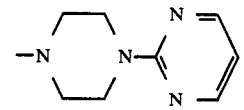

(d)

where $R_1$ is hydrogen or a halogen having an atomic number of from 9 to 35, or a pharmaceutically acceptable salt thereof.

2. A compound according to claim 1 wherein n is 3 or 4, and the two R moieties are taken together with the nitrogen to which they are bonded to indicate a

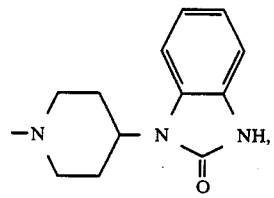

ring, or a pharmaceutically acceptable salt thereof.

3. A compound according to claim 2 where the compound is 2,4-dihydro-2-[3-[4-(2-pyrimidinyl)-1-piperazinyl]propyl]-1H-[1,2,4]triazolo[3,4-c][1,4]benzoxazin-1-one, or a pharmaceutically acceptable salt thereof.

4. A compound according to claim 1 wherein n is 3 or 4, and the two R moieties are taken together with the nitrogen to which they are bonded to complete a

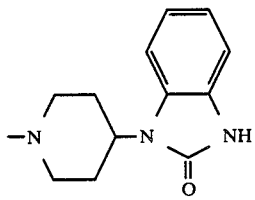

ring, or a pharmaceutically acceptable salt thereof.

5. A compound according to claim 4 wherein the compound is 2-[3-[4-(2,3-dihydro-2-oxo-1H-benzimidizol-1-yl)-1-piperidinyl]propyl]-2,4-dihydro-1H-[1,2,4]triazolo[3,4-c][1,4]benzoxazin-1-one, or a pharmaceutically acceptable salt thereof.

6. A compound according to claim 4 where the compound is 2-[4-[4-(2,3-dihydro-2-oxo-1H-benzimidazol-1-yl)piperidinyl]butyl]-2,4-dihydro-1H-[1,2,4]triazolo[3,4-c][1,4]benzoxazin-1-one, or a pharmaceutically acceptable salt thereof.

7. A compound according to claim 1 wherein n is 3 or 4, and the two R moieties are taken together with the nitrogen to which they are bonded
to complete a

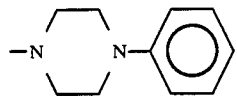

ring, where $R_1$ is hydrogen or a halogen having an atomic number of from 9 to 35 or a pharmaceutically acceptable salt thereof.

8. A compound according to claim 7 where the compound is 2,4-dihydro-2-[3-(4-phenylpiperazin-1-yl)propyl]-1H-[1,2,4]triazolo[3,4-c][1,4]benzoxazin-1-one, or a pharmaceutically acceptable salt thereof.

9. A compound according to claim 7 where the compound is 2,4-dihydro-2-[4-(4-phenylpiperazin-1yl)-butyl]-1H-[1,2,4]triazolo[3,4-c][1,4]benzoxazin-1-one, or a pharmaceutically acceptable salt thereof.

10. A compound according to claim 7 where the compound is 2-[4-[4-(3-chlorophenyl)-1-piperazinyl]-butyl]-2,4-dihydro-1H-[1,2,4]triazolo[3,4-c][1,4]benzoxazin-1-one, or a pharmaceutically acceptable salt thereof.

11. A compound according to claim 1 wherein n is 3 or 4, and the two R moieties are taken with the nitrogen to which they are bonded to complete a

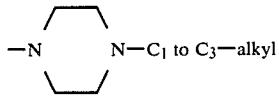

ring, or a pharmaceutically acceptable salt thereof.

12. A compound according to claim 11 where the compound is 2,4-dihydro-2-[4-(4-methylpiperazin-1-yl)butyl]-1H-[1,2,4]triazolo[3,4-c][1,4]benzoxazin-1-one, or a pharmaceutically acceptable salt thereof.

13. A composition useful in pharmaceutical dosage unit form for treating patients suffering from allergic or hypertensive conditions which comprises a compound according to claim 1 mixed with a pharmaceutical carrier.

14. A method for treating a human or valuable animal patient suffering allergic or hypertensive conditions which comprises administering to said patient an amount of a compound of claim 1 sufficient and effective for alleviating the allergic or hypertensive condition in said patient.

* * * * *